(12) United States Patent
Johnson

(10) Patent No.: US 6,230,043 B1
(45) Date of Patent: May 8, 2001

(54) METHOD AND APPARATUS FOR CAPTURING AND AUTOMATICALLY TRANSFERRING AN X-RAY IMAGE TO A REMOTE LOCATION

(75) Inventor: John A. Johnson, Delafield, WI (US)

(73) Assignee: General Electric Company, Milwaukee, WI (US)

(*) Notice: Subject to any disclaimer, the term of this patent is extended or adjusted under 35 U.S.C. 154(b) by 0 days.

(21) Appl. No.: 09/163,497

(22) Filed: Sep. 30, 1998

(51) Int. Cl.$^7$ .................................................. A61B 5/05
(52) U.S. Cl. ........................ 600/425; 600/443; 378/146; 378/62; 73/624; 346/33; 360/18
(58) Field of Search ..................... 600/437, 443, 600/425; 378/146, 62; 73/625; 346/33; 360/18

(56) References Cited

U.S. PATENT DOCUMENTS

| | | | |
|---|---|---|---|
| 4,457,311 | * | 7/1984 | Sorenson et al. ................. 600/447 |
| 4,993,025 | * | 2/1991 | Vesel et al. ....................... 370/450 |
| 5,447,153 | * | 9/1995 | Weil et al. ........................ 128/630 |
| 5,806,521 | * | 9/1998 | Morimoto et al. ................ 600/447 |

* cited by examiner

*Primary Examiner*—Marvin M. Lateef
*Assistant Examiner*—Jeoyuh Lin
(74) *Attorney, Agent, or Firm*—Barbara Joan Haushalter; Christian G. Cabou; Phyllis Y. Price

(57) ABSTRACT

A system and method for providing remote viewing and analysis of diagnostic images is provided by the present invention. Electronic diagnostic imaging equipment receives raw data from an operator, and means responsive to the raw data translates the data into scanner commands to acquire a scan. A remote terminal is adapted to receive the raw data and scan data, and to reproduce and manipulate images represented by the received data. In accordance with the present invention, these steps and functions can be rapidly achieved, so that the maximum amount of existing data required for image quality issue analysis is available.

9 Claims, 2 Drawing Sheets

METHOD AND APPARATUS FOR CAPTURING AND AUTOMATICALLY TRANSFERRING AN X-RAY IMAGE TO A REMOTE LOCATION

TECHNICAL FIELD

The present invention relates to the field of electronic monitoring and diagnosis. It finds particular application in conjunction with magnetic resonance imagers and will be described with particular reference thereto. However, it is to be appreciated that the invention may also find application in conjunction with other imaging/scanning apparatus, other medical electronic and computerized equipment, and the like.

BACKGROUND OF THE INVENTION

There are many situations wherein it is desired to produce diagnostic image information with respect to a subject by means of any of a variety of electronic apparatuses, and for then making the results of these diagnostic tests promptly available to a person who is not present at the diagnosis site. This can be true not just for analyzing certain results, but also when there are questions or concerns about the quality of an image acquired on a system. If an imaging system is exhibiting an image quality problem, it is necessary and desirable to correct the problem as quickly as possible, so that the problem extends to as few scans as possible.

In reviewing and/or correcting image quality problems, the user may need to request assistance from a remote source. In order to analyze and correct the problem, the remote source will usually require the data files associated with the problem period. However, imaging systems typically have temporary files. That is, all data associated with a certain scan or period of time, is deleted at some point, often before a service technician can be on site to access the data to help in troubleshooting image quality issues. Therefore, all data associated with a "problem" time is often lost before it can be retrieved and analyzed.

Currently, when magnetic imaging customers have questions or concerns about the quality of an image acquired on their system, they must request assistance from a Support Center. A Support Center engineer must then connect to that system and pull not only the image(s) in question for retrieval and analysis, but particularly the data files (error logs, scan protocols, crash files, raw data files, etc.), for retrieval and analysis at the Support Center. This process requires the engineer and the system operator, necessarily at separate locations (and, often, in separate time zones), to be available concurrently. Furthermore, this requires concurrent availability within a very immediate time frame, to prevent the loss of temporary files. Obviously, this may inconvenience the operator, requiring him or her to interrupt the scanning schedule to contact the Support Center, as well as possibly requiring availability of the engineer at an inconvenient time.

It is seen, therefore, that it would be desirable to provide a new and useful system and method for saving and transmitting to a remote site diagnostic information, system and data files, and images generated by an imaging modality at a subject-testing site.

BRIEF SUMMARY OF THE INVENTION

The present invention provides a novel system and method for immediate capture and forwarding of multiple images and data files to a remote location, such as to a Support Center, via an on-site transmitting means. The present invention, therefore, relates to systems for presenting to a remote viewer images corresponding to diagnostic image information, and particularly to such systems for doing so by means of rapidly acting computerized digital telecommunications apparatus. When invoked, the function according to the present invention, will capture and store a selected image(s), and information regarding the current system operating state. The resultant data file can be used later by either an on-site field engineer or transferred to a Support Center for remote analysis.

In accordance with one aspect of the present invention, a system and method for providing remote viewing and analysis of diagnostic images is provided. Electronic diagnostic imaging equipment receives raw data from an operator, and means responsive to the raw data translates the data into scanner commands to acquire a scan. A remote terminal is adapted to receive the raw data and scan data, and to reproduce and manipulate images represented by the received data. In accordance with the present invention, these steps and functions can be rapidly achieved, so that the maximum amount of existing data required for image quality issue analysis is available.

Accordingly, it is an object of the present invention to provide a new and useful system and method for transmitting to a remote site diagnostic data files, information and images generated by an imaging modality at a subject-testing site.

Other objects and advantages of the invention will be apparent from the following description, the accompanying drawings and the appended claims.

DETAILED DESCRIPTION OF THE INVENTION

Figure 1:
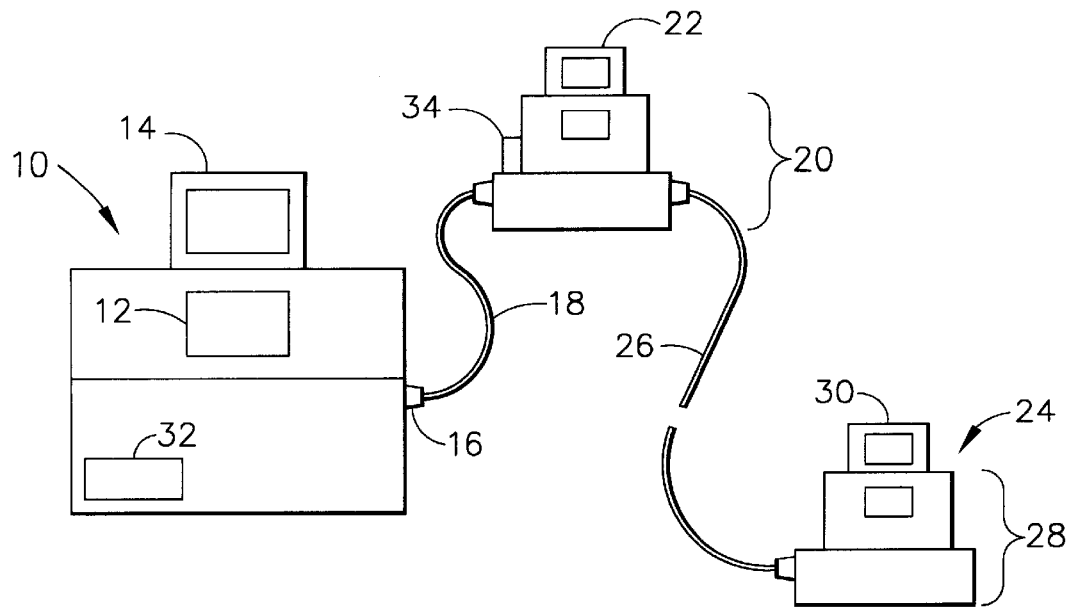
FIG. 1 is a schematic front elevational view of one embodiment of the physical arrangement of the system in accordance with the present invention.

Turning now to the specific embodiments of the invention illustrated in the drawings by way of example only, in FIG. 1 a diagnostic imaging apparatus 10 is shown which may be a standard original equipment manufacturer's apparatus, such as a magnetic resonance imager (MRI), a computerized tomography unit (CT Scanner), an ultrasound unit, or other medical or non-medical diagnostic imaging apparatus. The imaging apparatus 10 typically comprises its own main CRT display 12, and, on certain systems, an auxiliary monochrome CRT display 14 for displaying the image-representing signal displayed by the apparatus 10. A jack 16 on the scan apparatus 10 supplies a signal, such as a digital or an rf analog video signal to coaxial line 18.

Near the diagnostic imaging apparatus 10 is a diagnostic station processor 20, such as a personal computer, typically including certain custom internal circuit boards, as known in the art, for performing special functions relating to the scanning apparatus 10, and a separate video monitor 22.

Remote from the diagnostic station processor 20 is a remote terminal 24, connected to the station processor by a communication line 26. The communication line 26 may comprise two pairs of wires, so that the remote terminal 24 and the diagnostic station processor 20 can communicate with each other and so that the diagnostic station processor can send images generated by the diagnostic imaging apparatus 10 to the remote terminal 24. The remote terminal user can also communicate with the diagnostic station processor, for example with regard to receiving certain images. The remote terminal in this example comprises a computer 28, plus a separate video monitor 30, for viewing the images and receiving the data transmitted thereto.

Figure 2A:
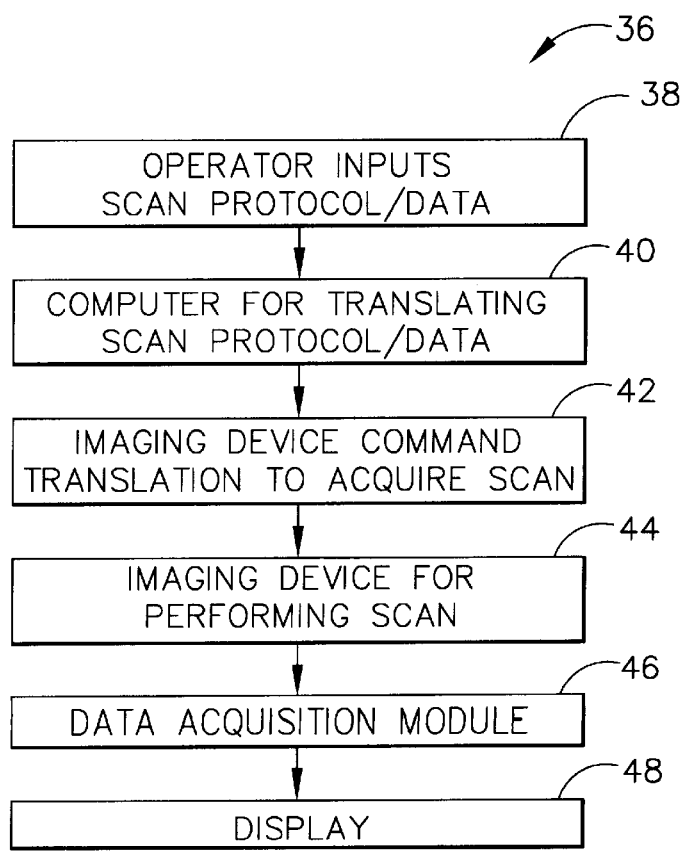
FIGS. 2A and 2B are flow chart block diagrams illustrating the steps for achieving the automatic capture and transfer of information from, for example, the diagnostic imaging apparatus of FIG. 1, in accordance with the present invention.
Figure 2B:
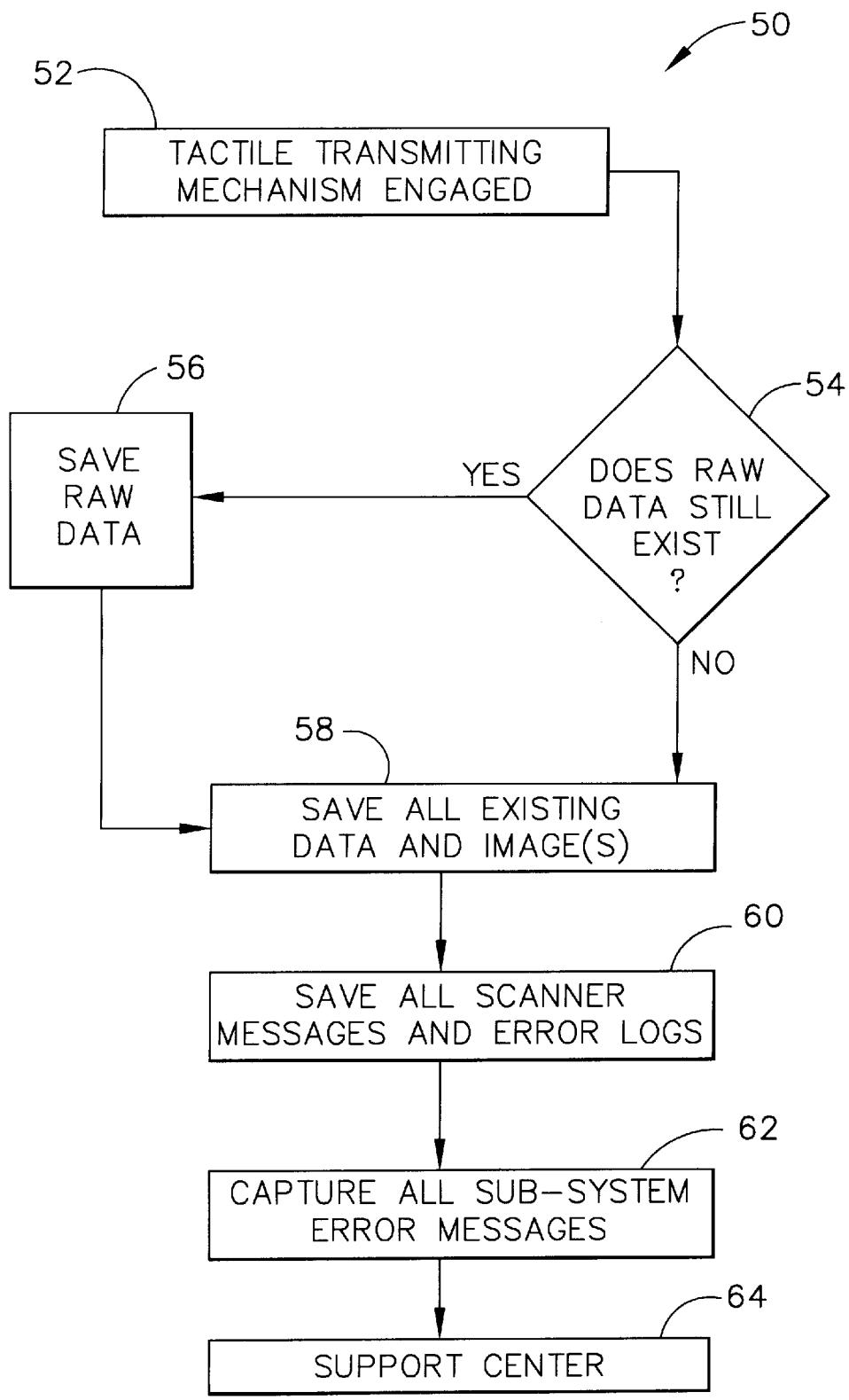

Referring now to FIGS. 2A and 2B, series of steps are illustrated for carrying out the function of the present invention, wherein a direct communication scheme provides immediate capture and forwarding of multiple images and data files from the diagnostic imaging apparatus 10 to the remote terminal 24, via an on-site transmitting means 32, such as a modem or internet access. The data file formats are usually either binary or ASCII, representing the digital image and raw data files. These files can later be displayed, reconstructed or manipulated, on site or at a remote location.

A tactile transmitting mechanism, such as button 34, is provided at the diagnostic station processor 20 to be invoked whenever the user, operator or field service engineer, located at the diagnostic imaging site, desires to forward one or more images and/or associated raw data to the remote terminal, such as a Support Center site, for examination. The diagnostic imaging apparatus 10 will automatically dial the remote terminal 24, verify a connection and transmit the images. Hence, raw data, in addition to the image data, may be captured and transmitted, before such temporary files are deleted from the system.

Referring now to FIG. 2A, the flow chart diagram 36 indicates the steps invoked to achieve the capture and/or transfer of images, in accordance with the present invention. Initially, a clinician enters the scan protocol for a particular scan into a central computer, as indicated at block 38. The computer, at block 40, then translates the protocol into imaging device (i.e., MRI, CT, etc.) commands, as indicated at block 42, to acquire the scan. The imaging device at block 44 then performs the scan. Analog scan data is sent to data acquisition module 46, which generates image data for display at block 48.

Turning now to FIG. 2B, and continuing with FIG. 2A, an "image snap shot", or capture and/or transfer of data illustrated in flow chart 50, may be invoked at block 52, in accordance with the present invention, when analysis and/or correction of an image quality problem is required. When tactile transmitting mechanism 34 from FIG. 1 is engaged, the flow chart moves to decision block 54 to determine if the raw data still exists, since the raw data would be the first item over-written on a scanner. If the raw data still exists, it is saved to a file or folder, as indicated at block 56, before proceeding to block 58. If the raw data is already overwritten, the flow chart moves directly to block 58, and saves all existing data, scan protocol used to generate the scan, and images(s) to the same file or folder. Additionally, all scanner messages and error logs are saved to the file or folder at block 60. All sub-system error messages from each sub-system, such as data acquisition block 46 of FIG. 2A, are captured to the same file or folder at block 62. Finally, the system initiates a call and sends (via any suitable means, such as a modem or internet access 32 of FIG. 1), all acquired information to a support center, as shown at block 64, for analysis of the problem.

When only an image is saved, because all other relevant information was over-written before the problem could be analyzed, critical information for diagnosing the image quality problem is missing. Often, the image itself does not include any useful information, beyond the fact that the image quality is poor. The error logs, scan protocols, crash files, raw data files, etc., provide the really useful information, insofar as providing a solution to the problem that occurred. With the "image snap shot" of the present invention, the maximum amount of useful information is saved before it is overwritten and lost, giving the engineer the best opportunity to solve image quality and system problems.

The invention has been described in detail with particular reference to certain preferred embodiments thereof, but it will be understood that modifications and variations can be effected within the spirit and scope of the invention.

What is claimed is:

1. A system for providing remote viewing and analysis of diagnostic images, comprising:
    electronic diagnostic imaging equipment for producing diagnostic image information;
    means for determining if the diagnostic image information is exhibiting an image quality problem;
    a remote terminal adapted to receive and save the diagnostic image information in a data file, and to reproduce and manipulate images represented by the received information; and
    means for reviewing the data file to correct the image quality problem.

2. A system as claimed in claim 1 further comprising a diagnostic station processor associated with the diagnostic imaging equipment for performing imaging functions, the diagnostic station processor connected to the remote terminal by a communication line.

3. A system as claimed in claim 2 wherein the communication line comprises multiple communication lines to allow the remote terminal and the diagnostic station processor to communicate with each other.

4. A system as claimed in claim 2 wherein the diagnostic station processor can send images generated by the diagnostic imaging equipment to the remote terminal.

5. A system as claimed in claim 1 wherein the remote terminal comprises a computer and a video monitor.

6. A method for securing an image snap shot of diagnostic images comprising the steps of:
    using an electronic apparatus to produce diagnostic image information with respect to a subject;
    determining if the diagnostic image information is exhibiting an image quality problem;
    collecting all information relative to any image quality problem period before the information is overwritten, to create a data file;
    saving a maximum amount of collected information for use in solving image quality and system problems;
    transmitting the data file to a remote site; and
    reviewing the data file to correct the image quality problem.

7. A method as claimed in claim 6 wherein the information collected comprises diagnostic data files, related information and images generated by the imaging system.

8. A method as claimed in claim 7 wherein the information collected comprises error logs, scan protocols, raw data, and crash files.

9. A method as claimed in claim 6 further comprising the step of providing a tactile transmitting mechanism for forwarding the data files to the remote site.

* * * * *